(12) United States Patent
Burck et al.

(10) Patent No.: US 9,150,599 B2
(45) Date of Patent: Oct. 6, 2015

(54) METHOD FOR THE SYNTHESIS OF N-(PHOSPHONOMETHYL)GLYCINE

(71) Applicant: STRAITMARK HOLDING AG, Zug (CH)

(72) Inventors: Sebastian Burck, Louvain-la-Neuve (BE); Patrick Notte, Wavre (BE)

(73) Assignee: STRAITMARK HOLDING AG, Zug (CH)

( * ) Notice: Subject to any disclaimer, the term of this patent is extended or adjusted under 35 U.S.C. 154(b) by 0 days.

(21) Appl. No.: 14/415,687

(22) PCT Filed: Jul. 17, 2013

(86) PCT No.: PCT/EP2013/065122
§ 371 (c)(1),
(2) Date: Jan. 19, 2015

(87) PCT Pub. No.: WO2014/012988
PCT Pub. Date: Jan. 23, 2014

(65) Prior Publication Data
US 2015/0175635 A1      Jun. 25, 2015

(30) Foreign Application Priority Data
Jul. 17, 2012 (EP) .................................... 12176751

(51) Int. Cl.
*C07F 9/113* (2006.01)
*C07F 9/38* (2006.01)

(52) U.S. Cl.
CPC ................................... *C07F 9/3813* (2013.01)

(58) Field of Classification Search
CPC ....................................................... C07F 9/4006
See application file for complete search history.

(56) References Cited

U.S. PATENT DOCUMENTS 4,084,499 A * 4/1978 Moehlenpah .................. 100/231
4,804,499 A * 2/1989 Miller et al. .................... 562/12

* cited by examiner

*Primary Examiner* — Sun Jae Yoo
(74) *Attorney, Agent, or Firm* — Brooks Kushman P.C.

(57) ABSTRACT

A method for the synthesis of N-(phosphonomethyl) glycine or one of its derivatives selected from the group of its salts, its phosphonate esters and its phosphonate ester salts, including the steps of: a) forming a reaction mixture having an acid catalyst, N,N'-bis(carboxymethyl)-2,5-diketopiperazine and a compound having one or more P—O—P anhydride moieties, wherein the moieties have one P atom at the oxidation state (+III) and the other P atom at the oxidation state (+III) or (+V), to form N,N'-bis(phosphonomethyl)-2,5-diketopiperazine, its dehydrated forms or their phosphonate esters; b) hydrolyzing the reaction mixture to form N-(phosphonomethyl)glycine or one of its derivatives selected from the group consisting of its salts, its phosphonate esters and its phosphonate ester salts.

18 Claims, No Drawings

METHOD FOR THE SYNTHESIS OF N-(PHOSPHONOMETHYL)GLYCINE

CROSS-REFERENCE TO RELATED APPLICATION

This application is the U.S. national phase of PCT Application No. PCT/EP2013/065122 filed on Jul. 17, 2013, which claims priority to EP Patent Application No. 12176751.1 filed on Jul. 17, 2012, the disclosures of which are incorporated in their entirety by reference herein.

FIELD OF THE INVENTION

The present invention is related to a novel method for the synthesis of N-(phosphonomethyl)glycine or one of its derivatives.

STATE OF THE ART

N-(phosphonomethyl)glycine, known in the agricultural chemical art as glyphosate, is a highly effective and commercially important broad spectrum phytotoxicant useful in controlling the growth of germinating seeds, emerging seedlings, maturing and established woody and herbaceous vegetation, and aquatic plants. Glyphosate is used as a systemic post-emergent herbicide to control the growth of a wide variety of annual and perennial grass and broadleaf weed species in cultivated crop lands, including cotton production.

Glyphosate and salts thereof are conveniently applied in aqueous herbicidal formulations, usually containing one or more surfactants, to the foliar tissues (i.e., the leaves or other photosynthesizing organs) of the target plant. After application, the glyphosate is absorbed by the foliar tissues and translocated throughout the plant. Glyphosate noncompetitively blocks an important biochemical pathway that is common to virtually all plants. More specifically, glyphosate inhibits the shikimic acid pathway that leads to the biosynthesis of aromatic amino acids. Glyphosate inhibits the conversion of phosphoenolpyruvic acid and 3-phosphoshikimic acid to 5-enolpyruvyl-3-phosphoshikimic acid by inhibiting the enzyme 5-enolpyruvyl-3-phosphoshikimic acid synthase (EPSP synthase or EPSPS) found in plants.

There are several well known manufacturing routes by which glyphosate can be prepared, for example the chemical pathways set out in U.S. Pat. No. 3,969,398; CA patent 1,039,739; U.S. Pat. Nos. 3,799,758; 3,927,080; 4,237,065 and U.S. Pat. No. 4,065,491, but all of these pathways present several drawbacks including product wastage, environmental problems and on top of that undesirable results from an economical point of view.

A major manufacturing pathway is based on the phosphonomethylation of a carboxymethylated carbamoyl compound.

WO9835930 patent application discloses a process for the preparation of an N-acetyl amino carboxylic acid by means of a carboxymethylation reaction. In this reaction, a reaction mixture is formed which contains a base pair, carbon monoxide, hydrogen and an aldehyde, particularly formaldehyde. The base pair is formed by the reaction of a carbamoyl compound and a carboxymethylation catalyst precursor. In general the carbamoyl compound is an amide, an urea or a carbamate; the carboxymethylation catalyst precursor may be any composition which is known to be useful in the carboxymethylation reactions and which generally contain a metal from group VIII of the periodic table. In a preferred embodiment, the carbamoyl compound and aldehyde are selected to yield an N-acetyl amino carboxylic acid which is readily converted to N-(phosphonomethyl)glycine, or a salt or ester thereof, through reaction with a phosphorous source and a aldehyde source. For the particular case where acetamide is converted into N-acetyl iminodiacetic acid through carboxymethylation, hydrolysis and phosphonomethylation of N-acetyl iminodiacetic acid results in the formation of N-(phosphonomethyl)iminodiacetic acid, which thereupon is oxidized, in the presence of a carbon or a platinum on carbon catalyst, to yield N-(phosphonomethyl)glycine. On the other hand N-acetyl iminodiacetic acid can cyclodimerize with the formation of N,N' bis(carboxymethyl)-2,5-diketopiperazine and acetic acid. N,N' bis(carboxymethyl)-2,5-diketopiperazine then is further reacted with a phosphorous acid source and a formaldehyde source to form N-(phosphonomethyl) iminodicarboxylic acid, which thereupon is oxidized, in the presence of a carbon or a platinum on carbon catalyst, to yield N-(phosphonomethyl)glycine.

WO0009520 patent application discloses a process wherein N-acetyliminodiacetic acid is formed via a continuous amidocarboxymethylation reaction. In this reaction, N-(acetyl)iminodiacetic acid is formed in an amidocarboxymethylation reactor system into which a source of each of the following is continuously fed: (1) acetamide or an acetamide derivative (2) formaldehyde or a formaldehyde generator or derivative (3) a carbonylation catalyst (4) carbon monoxide and optionally (5) hydrogen. The N-(acetyl)iminodiacetic acid is either: (1) reacted with a source of phosphorous and a source of formaldehyde in the presence of an acid to form a phosphonomethylation reaction product containing N-(phosphonomethyl)iminodiacetic acid and acetic acid, or (2) deacylated and cyclized to form a 2,5-diketopiperazine derivative and then reacted with a source of phosphorous and a source of formaldehyde in the presence of an acid to form a phosphonomethylation reaction product containing N-(phosphonomethyl)iminodiacetic acid and acetic acid. Either way, the N-(phosphonomethyl)iminodiacetic acid is precipitated and the precipitate is recovered.

WO0192208 patent application discloses a process for the preparation of amino carboxylic acids, N-acetyl amino carboxylic acids, or derivatives thereof by carboxymethylation of an amide, amide precursor or amide source compound in the presence of a carboxymethylation catalyst precursor, which generally contains a metal from Group VIII of the periodic table, and which preferably comprises cobalt, and a promoter. In a preferred embodiment, the promoter is a supported noble metal promoter. A carboxymethylation reaction mixture is formed by introducing a promoter, an amide, amide precursor or amide source compound, carbon monoxide, hydrogen, an aldehyde or an aldehyde source compound and a carboxymethylation catalyst precursor into a carboxymethylation reaction zone. In another preferred embodiment, the amide compound and aldehyde are selected to yield an N-acetyl amino carboxylic acid which is readily converted to N-(phosphonomethyl)glycine, or a salt or an ester thereof.

In WO9835930, WO0009520 and WO0192208 patent applications, N-(phosphonomethyl)glycine may be prepared from phosphonomethylation either of N-acetyl amino acetic acid or of N-acetyliminodiacetic acid or of N,N'-bis(carboxymethyl)-2,5-diketopiperazine, obtained from cyclodimerization of N-acetyliminodiacetic acid. When N,N'-bis(carboxymethyl)-2,5-diketopiperazine is concerned the phosphonomethylation can be done on the N,N'-bis(carboxymethyl)-2,5-diketopiperazine straight on or on the aminodiacetic acid obtained from hydrolysis of N,N'-bis(carboxymethyl)-2,5-diketopiperazine. Besides N-(phosphonomethyl)glycine, acetic acid, formaldehyde and carbon dioxide are formed Cyclodimerization of iminodiacetic acid or its derivatives already is subject to a number of publications.

The cyclization reaction of iminodiacetic acid in an ethanol/water solution in the presence of nickel (II) chloride is reported by Silva and coworkers in *Acta Crystallographica* 2003, C59, pages 562-563. After 16 hours at 60° C., the solution was left to cool and evaporate slowly at room temperature to generate small single crystals of 2,5-diketopiperazine-1,4-diacetic acid.

The transformation of iminodiacetic acid into 2,5-diketopiperazine-1,4-diacetate in the presence of oxalic acid, nitric acid and $Ln_2O_3$ (wherein Ln=Dy, Ho, Er or Yb) in water was observed during the synthesis of lanthanide-based 3D coordination polymers as reported by Kong et al. in *Dalton Transactions*, 2009, pages 1707-1709. The intermolecular dehydration coupling of iminodiacetic acid is performed at 180° C. for 100 hours.

Zang et al. report the cyclodimerization of iminodiacetic acid, in the presence of phosphoric acid, in *Hecheng Huaxue* 2008, 1, page 72. A reaction time of 12 hours at 170° C. is disclosed.

In *Heterocycles* 1997, 45, page 1679, Tapia-Benavidis et al. report the cyclodimerization of iminodiacetic acid in toluene in the presence of triethylborane.

In WO9835930, WO0009520 and WO0192208 patent applications cyclodimerization of N-acetylglycine and N-acetyl iminodiacetic acid to 2,5-diketopiperazine and N,N'-bis(carboxymethyl)-2,5-diketopiperazine respectively, is performed at a temperature comprised between about 100° C. and about 250° C.

When N,N'-bis(carboxymethyl)-2,5-diketopiperazine intermediate is prepared, phosphonomethylation results in the formation of N-(phosphonomethyl)iminodiacetic acid which in a subsequent step is oxidized to N-(phosphonomethyl)glycine, formaldehyde and carbon dioxide.

WO2006107824 patent application relates to the preparation of N-(phosphonomethyl)glycine from N-(phosphonomethyl)iminodiacetic acid, and more particularly to methods for control of the conversion of N-(phosphonomethyl)iminodiacetic acid, for the identification of reaction end points relating to N-(phosphonomethyl)iminodiacetic acid conversion and the preparation of glyphosate products having controlled N-(phosphonomethyl)iminodiacetic acid content.

U.S. Pat. No. 3,969,398 discloses a process for the production of N-(phosphonomethyl)glycine by the oxidation of N-(phosphonomethyl)iminodiacetic acid utilizing a molecular oxygen-containing gas as the oxidant in the presence of a catalyst consisting essentially of activated carbon.

U.S. Pat. No. 4,624,937 discloses an improved process for the selective production of secondary amines and primary amines by bringing together under reaction conditions a tertiary amine or a secondary amine with oxygen or an oxygen-containing gas in the presence of an activated carbon catalyst, the improvement which comprises using an activated carbon catalyst wherein oxides have been removed from the surface of the carbon. The influence of the two-step treatment of the carbon catalyst on the formation of N-(phosphonomethyl) glycine out of N,N'-bis(phosphonomethyl)iminodiacetic acid is illustrated.

AIMS OF THE INVENTION

The present invention aims to provide an improved, more preferably an efficient and environmental-friendly method for the manufacture of N-(phosphonomethyl)glycine or one of its derivatives, which does not present the drawbacks of the methods of the state of the art.

SUMMARY OF THE INVENTION

The present invention discloses a method for the synthesis of N-(phosphonomethyl)glycine or one of its derivatives selected from the group consisting of its salts, its phosphonate esters and its phosphonate ester salts, comprising the steps of:

a) forming a reaction mixture comprising an acid catalyst, N,N'-bis(carboxymethyl)-2,5-diketopiperazine and a compound comprising one or more P—O—P anhydride moieties, wherein said moieties comprise one P atom at the oxidation state (+III) and the other P atom at the oxidation state (+III) or (+V), to form N,N'-bis(phosphonomethyl-2,5-diketopiperazine, its dehydrated forms or their phosphonate esters;

b) hydrolyzing the reaction mixture to form N-(phosphonomethyl)glycine or one of its derivatives selected from the group consisting of its salts, its phosphonate esters and its phosphonate ester salts.

Preferred embodiments of the present invention disclose one or more of the following features:

in step a), the compound comprising a P—O—P anhydride moiety, having one P atom at the oxidation state (+III) and the other P atom at the oxidation state (+III) or (+V), is gradually mixed, into a mixture comprising N,N'-bis (carboxymethyl)-2,5-diketopiperazine and an acid catalyst, while maintaining the temperature below 120° C., preferably below 90° C., more preferably below 80° C.;

the P—O—P anhydride moiety comprising compound is selected from the group consisting of:

tetraphosphorus hexaoxide, tetraethylpyrophosphite;

the P—O—P anhydride moiety comprising compound obtained from the combination of one or more compounds comprising one or more P—OH moieties with one or more compounds comprising one or more P—O—P anhydride moieties, wherein the P atom of one or more compounds is at the oxidation state (+III);

the P—O—P anhydride moiety comprising compound obtained from the combination of one or more compounds comprising one or more P—OH moieties with one or more compounds comprising one or more P—X moieties, wherein the P atom of one or more compounds is at the oxidation state (+III);

the P—O—P anhydride moiety comprising compound obtained from the combination of one or more compounds having one or more P—X moieties and water, wherein the P atom of the P—X moiety comprising compound is at the oxidation stage (+III);

the P—O—P anhydride moiety comprising compound obtained from the combination of one or more compounds having 2 or more P—O—P moieties and water, wherein the P—O—P moiety comprising compound has P atom at the oxidation state (+III) and one P atom at the oxidation state (+III) or (+V);

wherein the compounds having one or more P—OH moieties may be accessible by tautomerization of a >P(=O)H moiety, wherein X is a halogenide selected from the group consisting of chlorine, bromine and iodine and.

wherein the halogen level is 1000 ppm or less, preferably 500 ppm or less and more preferably 200 ppm or less, expressed in relation to the P—O—P anhydride moiety comprising compound;

the P—O—P anhydride moiety comprising compound is selected from the group consisting of tetraphosphorus hexaoxide, tetraethylpyrophosphite, and the P—O—P anhydride moiety comprising compound obtained from the combination of phosphorous acid and tetraphosphorus hexaoxide, of phosphorous acid and tetraphosphorus decaoxide, of phosphorous acid and phosphorus trichloride, of dimethylphosphite and tetraphosphorus decaoxide, of phosphorus trichloride and water and of tetraphosphorus hexaoxide and water;

the P—O—P anhydride moiety comprising compound is tetraphosphorus hexaoxide;

the acid catalyst is a homogeneous Brønsted acid catalyst preferably selected from the group consisting of methanesulfonic acid, trifluoromethanesulfonic acid, acetic acid, trifluoroacetic acid, p-toluenesulfonic acid, hydrochloric acid, phosphorous acid, phosphoric acid and hypophosphorous acid and mixtures thereof.

the acid catalyst is a heterogeneous Brønsted acid catalyst selected from the group consisting of:
(i) solid acidic metal oxide combinations as such or supported onto a carrier material;
(ii) cation exchange resins selected from the group comprising copolymers of styrene, ethylvinyl benzene and divinyl benzene, functionalized so as to graft $SO_3H$ moieties onto the aromatic group and perfluorinated resins carrying carboxylic and/or sulfonic acid groups;
(iii) organic sulfonic, carboxylic and phosphonic Brønsted acids (which are substantially immiscible in the reaction medium at the reaction temperature);
(iv) an acid catalyst derived from:
the interaction of a solid support having a lone pair of electrons onto which is deposited an organic Brønsted acid; or
the interaction of a solid support having a lone pair of electrons onto which is deposited a compound having a Lewis acid site; or
heterogeneous solids functionalized by chemical grafting with a Brønsted acid group or a precursor therefore; and
(v) heterogeneous heteropolyacids of the general formula $H_xPM_yO_z$ wherein P is selected from phosphorus and silicon and M is selected from tungsten and molybdenum and combinations thereof.

the acid catalyst is a Lewis acid catalyst selected from the group consisting of $LiN(CF_3SO_2)_2$, $Mg(OCF_3SO_2)_2$, $Al(OCF_3SO_2)_3$, $Bi(OCF_3SO_2)_3$, $Sc(OCF_3SO_2)_3$.

the acid catalyst is trifluoromethanesulfonic acid.

the reaction mixture of step a) comprises a solvent selected from the group consisting of ethylacetate, acetonitrile, 1,4-dioxane, sulfolane, toluene, paraffin, aliphatic and aromatic halogenated hydrocarbons, such as tetrachloroethane, trichloroethylene, tetrachloroethylene, carbon tetrachloride, o-chlorotoluene, dichlorobenzene and monochlorobenzene, 1-ethyl-3-methyl-imidazolium bis(trifluoromethylsulfonyl)imide or a mixture thereof.

step a), after completion of the mixing of the compound comprising a P—O—P anhydride moiety, having one P atom at the oxidation state (+III) and the other P atom at the oxidation state (+III) or (+V), the N,N'-bis(carboxymethyl)-2,5-diketopiperazine, the acid catalyst and optionally the solvent, is maintained at a temperature comprised between 30° C. and 120° C., preferably between 40° C. and 100° C. for a period of time comprised between 10 minutes and 72 hours, preferably comprised between 1 hour and 30 hours.

the hydrolysis of step b) is performed under acid conditions at a temperature comprised between 25° C. and 250° C., preferably between 80° C. and 200° C. for a period of time comprised between 10 and 100 hours, preferably between 1 and 50 hours.

the equivalent ratio of N,N'-bis(carboxymethyl)-2,5-diketopiperazine to P—O—P anhydride moiety is comprised between 0.2 and 2.5, preferably between 0.3 and 2.0 and more preferably between 0.5 and 1.5.

the molar ratio of N,N'-bis(carboxymethyl)-2,5-diketopiperazine to tetraphosphorus hexaoxide is comprised between 0.4 and 5.0, preferably between 0.6 and 4.0 and more preferably between 1.0 and 3.0.

the molar ratio of the acid catalyst to the N,N'-bis(carboxymethyl)-2,5-diketopiperazine is comprised between 0.05 and 25.0, preferably between 0.1 and 20.0.

carbon monoxide, formed in step a), is recovered and reused.

the derivatives of N-(phosphonomethyl)glycine are selected from the group consisting of N-(phosphonomethyl)glycine salts, phosphonate esters of N-(phosphonomethyl) glycine and phosphonate esters of N-(phosphonomethyl)glycine salts and wherein the cation of the salt is selected from the group consisting of ammonium, isopropylammonium, ethanolammonium, dimethylammonium, trimethylsulphonium, sodium and, potassium;

N-(phosphonomethyl)glycine is obtained in a batch or a continuous process.

DETAILED DESCRIPTION OF THE INVENTION

The present invention provides an economical and preferably environmental friendly method for the manufacture of N-(phosphonomethyl)glycine or one of its derivatives. Under derivatives the present invention understands salts and phosphonate esters of N-phosphonomethylglycine.

The N-(phosphonomethyl)glycine salts comprise the carboxylate and/or (di) phosphonate anion and an agronomically acceptable cation or the ammonium cation of N-(phosphonomethyl)glycine and a agronomically acceptable anion.

Preferred salts are the ammonium, the isopropylammonium, the ethanolammonium, the dimethylammonium, the trimethylsulfonium, the sodium and the potassium salts wherein the ratio of the cation to the N-(phosphonomethyl) glycine anion is comprised between 0.1 and 3.0.

When hydrolysis is performed under base conditions, the salt comprises the carboxylate and/or phosphonate anion of N-(phosphonomethyl)glycine and an alkali metal, alkaline earth metal or ammonium cation; otherwise, when hydrolysis is performed under acid conditions, the formed salt comprises the ammonium cation from N-(phosphonomethyl)glycine and the anion coming from the acid used for the hydrolysis. In this particular last case, the anion is for example the chloride anion, coming from hydrochloric acid, or the sulfate anion coming from sulfuric acid.

The phosphonate esters comprise one or more substituted or unsubstituted hydrocarbyl groups which may be branched or unbranched, saturated or unsaturated and may contain one or more rings. Suitable hydrocarbyls include alkyl, alkenyl, alkynyl and aryl moieties. They also include alkyl, alkenyl, alkynyl and aryl moieties substituted with other aliphatic or cyclic hydrocarbyl groups, such as alkaryl, alkenaryl and alkynaryl.

The substituted hydrocarbyl is defined as a hydrocarbyl wherein at least one hydrogen atom has been substituted with an atom other than hydrogen such as an halogen atom, an oxygen atom to form for example an ether or an ester, a nitrogen atom to form an amide or nitrile group or a sulfur atom to form for example a thioether group.

Phosphonate esters in general are prepared in step a), by using the P—O—P anhydride moiety comprising compound substituted with the corresponding hydrocarbyl substituents.

The derivatives of N-phosphonomethylglycine can be obtained as such as an outcome of the hydrolysis reaction step b) or obtained by further treatment of N-(phosphonomethyl) glycine.

Under derivatives the present invention understands salts, phosphonate esters, or phosphonate ester salts of N-(phosphonomethyl)glycine.

In the present invention it is understood that the expression N-(phosphonomethyl)glycine comprises all derivatives.

The method of the present invention includes the steps of:
a) reacting N,N'-bis(carboxymethyl)-2,5-diketopiperazine with a P—O—P anhydride moiety comprising compound, having one P atom at the oxidation state (+III) and the other P atom at the oxidation state (+III) or (+V), in the presence of an acid catalyst and optionally a solvent, to form N,N'-bis (phosphonomethyl)-2,5-diketopiperazine, its dehydrated forms or their derivatives;
b) hydrolyzing the formed N,N'-bis(phosphonomethyl)-2,5-diketopiperazine, its dehydrated forms or their derivatives to obtain the N-(phosphonomethyl)glycine or one of its derivatives.

N,N'-bis(carboxymethyl)-2,5-diketopiperazine may be obtained from cyclodimerization of iminodiacetic acid While the P—O—P anhydride moiety comprising compound preferably is selected from the group consisting of tetraphosphorus hexaoxide and partially hydrolysed species of tetraphosphorus hexaoxide obtained through reaction of 1 mole of tetraphosphorus hexaoxide with 1, 2, 3, 4 and 5 moles of water respectively, it is understood that all compounds comprising at least one P—O—P anhydride moiety wherein one P atom is at the oxidation state (+III) and the other P atom is at the oxidation state (+III) or (+V) can be used for the purpose of the invention.

Suitable P—O—P anhydride moiety comprising compounds can either comprise a P—O—P anhydride moiety in the compound itself (e.g. $P_4O_6$ or pyrophosphites $(RO)_2P$—O—$P(OR)_2$) or be generated in situ by combining reagents that will form the necessitated P—O—P anhydride moiety upon combination before reacting with the N,N'-bis(carboxymethyl)-2,5-diketopiperazine.

Suitable reagent combination are
a) compounds containing a least one P—OH moiety (also accessible by tautomerisation of a >P(═O)H moiety into >P(LP)OH (where LP stands for lone pair of electrons) as possible for dimethylphosphite $(MeO)_2P(═O)H$) and compounds containing at least one P—O—P anhydride moiety e.g. $P_2O_5$ or $P_4O_6$;
b) compounds containing at least one P—OH moiety and compounds containing at least one P—X (X═Cl, Br, I) moiety;
c) compounds containing at least one P—X moiety and $H_2O$ or
d) compounds containing P—O—P anhydride moieties and $H_2O$ for partial hydrolysis.

In case a) and b) it is mandatory that at least in one of the utilised compounds the P atom is in the oxidation state (+III) whereas in case c) the P atom has to be in the oxidation state (+III) and in case d) the P—O—P moieties have one P atom at the oxidation state (+III) and the other P atom at the oxidation state (+III) or (+V), in order to form the P—O—P anhydride moiety comprising compound, having one P atom at the oxidation state (+III) and the other P atom at the oxidation state (+III) or (+V).

P—O—P anhydride moiety comprising compounds wherein the P—O—P anhydride moiety is already present are phosphorus oxides with the formula $P_4O_n$ with n=6-9, pyrophosphites with the general formula $(RO)_2P$—O—$P(OR)_2$ wherein R is an alkyl or aryl group, pyrophosphorous acid $(H_4P_2O_5)$ and isohypophosphoric acid $(H)(HO)P(O)$—P—P $(O)(OH)_2)$.

Combinations described under a) are obtained by reacting e.g. phosphorus oxides with formula $P_4O_n$ with n=6-10, alkyl substituted pyrophosphites, pyrophosphorous acid, isohypophosphoric acid, metaphosphoric acid or polyphosphoric acid with phosphorous acid, phosphoric acid, mono or disubstituted phosphites with formula $(RO)PO_2H_2$ or $(RO)_2POH$ wherein R is an alkyl or aryl group, phosphate esters (RO) $PO_3H_2$ or $(RO)_2PO_2H$, phosphonic acids $RPO_3H_2$ or its monoester $RPO_2H(OR)$ with the proviso that such combinations will lead to P—O—P anhydride moiety comprising compounds having one P atom at the oxidation state (+III) and the other P atom at the oxidation state (+III) or (+V).

Combinations described under b) are obtained by combining $PCl_3$, $PBr_3$, $P(O)Cl_3$, mono or dichloro phosphites like $(RO)_2PCl$ and $(RO)PCl_2$ with phosphorous acid, phosphoric acid, mono or disubstituted phosphites with formula (RO) $PO_2H_2$ or $(RO)_2POH$ with the proviso that such combinations will lead to P—O—P anhydride moiety comprising compound having one P atom at the oxidation state (+III) and the other P atom at the oxidation state (+III) or (+V).

Combinations described under c) are obtained by combining $PCl_3$, $PBr_3$, mono or dichloro phosphites like $(RO)_2PCl$ and $(RO)PCl_2$ with $H_2O$.

In order to obtain a P—O—P anhydride moiety comprising compounds free of P—X functions the remaining P—X functions are hydrolysed with water. Remaining P—O—P anhydride moieties can also be hydrolysed as long as the required P—O—P anhydride moiety wherein one P atom is at the oxidation state (+III) and the other P atom is at the oxidation state (+III) or (+V) remains.

Most preferred are tetraphosphorus hexaoxide, tetraethylpyrophosphite and the combinations of phosphorous acid and tetraphosphorus hexaoxide, of phosphorous acid and tetraphosphorus decaoxide, of phosphorous acid and phosphorus trichloride, of dimethylphosphite and tetraphosphorus decaoxide, of phosphorus trichloride and water and of tetraphosphorus hexaoxide and water The amount of 'reactive' P(+III) atoms that can be converted into phosphonic acids according to this invention is determined by the amount of P(+III) atoms and the amount of P—O—P anhydride moieties. If there are more P—O—P anhydride moieties than P(+III) atoms then all P(+III) atoms are converted into phosphonic acids. If there are less P—O—P anhydride moieties than P(+III) atoms then only a part of P(III) atoms equal to the amount of P—O—P anhydride moieties is converted into phosphonic acids.

In the event halogen containing starting materials, e.g. $PCl_3$, $POCl_3$ or $PBr_3$ are used, the level of halogen in the P—O—P anhydride comprising compound shall be kept below 1000 ppm, usually below 500 ppm, preferably below 200 ppm, expressed in relation to the P—O—P material being 100%. Therefore, all excess P—X functions are hydrolysed before the reactions with the substrate by addition of one molecule of $H_2O$ per excess P—X function. The formed HX is removed by e.g. blowing a dry inert gas, like nitrogen or helium, through the solution.

The tetraphosphorus hexaoxide preferably used within the scope of the present invention may be represented by a substantially pure compound containing at least 85%, preferably more than 90%, more preferably at least 95% and in one particular execution at least 97% of $P_4O_6$. While tetraphosphorus hexaoxide, suitable for use within the context of this invention, may be manufactured by any known technology, in preferred executions it is prepared in accordance with the method described in WO 2009/068636 and/or WO 2010/055056 patent applications under the section entitled "Process for the manufacture of $P_4O_6$ with improved yield". In detail, oxygen, or a mixture of oxygen and inert gas, and gaseous or liquid phosphorus are reacted in essentially stoichiometric amounts in a reaction unit at a temperature in the range from 1600 to 2000 K, by removing the heat created by the exothermic reaction of phosphorus and oxygen, while maintaining a preferred residence time of from 0.5 to 60 seconds followed by quenching the reaction product at a temperature below 700 K and refining the crude reaction product by distillation. Tetraphosphorus hexaoxide so prepared is a pure product containing usually at least 97% of the oxide. The so produced $P_4O_6$ is generally represented by a liquid material of high purity containing in particular low levels of elementary phosphorus, $P_4$, preferably below 1000 ppm, expressed in relation to the $P_4O_6$ being 100%. The preferred residence time is from 5 to 30 seconds, more preferably from 8 to 30 seconds. The reaction product can, in one preferred execution, be quenched to a temperature below 350 K.

It is presumed that the $P_4O_6$ participating in a reaction at a temperature of from 24° C. (melting t°) to 120° C. is necessarily liquid or gaseous although solid species can, academically speaking, be used in the preparation of the reaction medium.

For reasons of convenience and operational expertise, the tetraphosphorus hexaoxide, represented by $P_4O_6$, is of high purity and contains very low levels of impurities, in particular elemental phosphorus, $P_4$, at a level below 1000 ppm, usually below 500 ppm and preferably not more than 200 ppm, expressed in relation to the $P_4O_6$ being 100%.

The acid catalyst used within the scope of the present invention is preferably a homogeneous Brønsted acid catalyst, optionally in the presence of solvent, or a heterogeneous Brønsted acid catalyst, in the presence of solvent, or a Lewis acid catalyst, in the presence of solvent.

On the other hand the Brønsted acid catalyst may be the solvent and catalyst at the same time; in order to be a suitable Brønsted catalyst, the solvent must be characterized by a pKa of less than 5.

The homogeneous Brønsted acid catalyst preferably is selected from the group consisting of methanesulfonic acid, fluoromethanesulfonic acid, trichloromethanesulfonic acid, trifluoromethanesulfonic acid, acetic acid, trifluoroacetic acid, tert-butyl-sulfonic acid, p-toluenesulfonic acid, naphthalene sulfonic acid, 2,4,6-trimethylbenzene-sulfonic acid, perfluoro or perchloro sulfonic acids, perfluoro or perchloro carboxylic acids, hydrochloric acid, hydrobromic acid, hydroiodic acid, phosphorous acid, phosphoric acid, and mixtures thereof. The homogeneous Brønsted acid is preferably methanesulfonic acid.

The heterogeneous Brønsted acid catalyst is preferably selected from the group of:
(i) solid acidic metal oxide combinations as such or supported onto a carrier material;
(ii) cation exchange resins selected from the group comprising copolymers of styrene, ethylvinyl benzene and divinyl benzene, functionalized so as to graft $SO_3H$ moieties onto the aromatic group and perfluorinated resins carrying carboxylic and/or sulfonic acid groups;
(iii) organic sulfonic, carboxylic and phosphonic Brønsted acids (which are substantially immiscible in the reaction medium at the reaction temperature);
(iv) an acid catalyst derived from:
the interaction of a solid support having a lone pair of electrons onto which is deposited an organic Brønsted acid; or
the interaction of a solid support having a lone pair of electrons onto which is deposited a compound having a Lewis acid site; or
heterogeneous solids functionalized by chemical grafting with a Brønsted acid group or a precursor therefore; and
(v) heterogeneous heteropolyacids of the general formula $H_xPM_yO_z$ wherein P is selected from phosphorus and silicon and M is selected from tungsten and molybdenum and combinations thereof.

The heterogeneous Brønsted acid catalyst for use in the method of the present invention is preferably selected from the group consisting of macroreticular polymeric resins, representing a continuous open pore structure and comprising sulfonic, carboxylic and/or phosphonic acid moieties.

The heterogeneous Brønsted acid catalyst is substantially insoluble or immiscible in the reaction medium. The catalyst can form, at the reaction conditions, in particular the reaction temperature, a second liquid phase and can be recovered at the end of the reaction by conventional techniques such as filtration or phase separation.

Homogeneous Brønsted acid catalysts can leave a residue within the final reaction product. Nevertheless, there are known techniques for recovering the acid catalyst from the reaction medium such as ion exchange, nano filtration or electrodialysis which can be used to solve or mitigate the problems. Alternatively the end product can be separated e.g. by precipitation using a co-solvent and the Brønsted catalyst recovered and recycled after removal of the co-solvent.

The Lewis acid for being included in the solvent in general is a homogeneous or heterogeneous Lewis acid.

Brønsted acidic solvents can be replaced by Lewis acids dissolved or suspended in an organic solvent.

Preferred homogeneous Lewis acids can be selected from metal salts having the general formula:

$$MX_n$$

wherein M represents a main group element or transition metal like Li, B, Mg, Al, Bi, Fe, Zn, La, Sc, Yb, or Pd; X in $MX_n$ is typically an anion of an acid or acid derivative like Cl, OTf or $NTf_2$, where Tf stands for $CF_3SO_2$ and n is equal to the oxidation state of M, which can be from 1 to 5. Possible combinations are e.g. $LiNTf_2$, $Mg(OTf)_2$, $MgCl_2$, $ZnCl_2$, $PdCl_2$, $Fe(OTf)_3$, $Al(OTf)_3$, $AlCl_3$, $Bi(OTf)_3$, $BiCl_3$, $Sc(OTf)_3$, $Ln(OTf)_3$, $Yb(OTf)_3$.

Preferably, combinations of a hard metal or a metal on the borderline between hard and soft according to the HSAB (hard soft acid base) concept like Li, Mg, Al, Sc, Zn, Bi, and weakly coordinating anions like OTf or $NTf_2$ are used. Examples of such preferred combinations are: $LiNTf_2$, $Mg(OTf)_2$, $Al(OTf)_3$, $Bi(OTf)_3$.

Preferred heterogeneous Lewis acids can be represented by species of discretionary selected subclasses created by interaction/bonding of homogeneous Lewis acids e.g. metal complexes, metal salts or organometallic species with polymeric organic or inorganic backbones. An example of such subclass is a polystyrene matrix with bonded $Sc(OTf)_2$ groups. Such catalyst can be prepared e.g. by interaction of a polystyrene sulfonic acid resin e.g. Amberlyst 15 with Sc(OTf)$_3$. The number of equivalents of Lewis acid functions can be determined in this case by different ways e.g. by acid base determination of the unreacted sulfonic acid groups, by quantitative determination of the liberated triflic acid and by ICP measurement of the amount of Sc on the resin.

Typical examples of suitable organic solvents are: anisole; chlorinated and fluorinated hydrocarbons such as fluorobenzene, chlorobenzene, tetrachloroethane, tetrachloroethylene, dichloroethane, dichloromethane; polar solvents like diglyme, glyme, diphenyloxide, polyalkylene glycol derivatives with capped OH groups such as OR* where R* is a low alkyl or acyl group; aliphatic hydrocarbons such as hexane, heptane, cyclohexane; non-cyclic ethers like dibutyl ether, diethyl ether, diisopropyl ether, dipentylether, and butylmethylether; cyclic ethers like tetrahydrofuran, dioxane and tetrahydropyran; mixed cyclic/non-cyclic ethers like cyclopentylmethylether; cyclic and non-cyclic sulfones like sulfolane; aromatic solvents like toluene, benzene, xylene; organic acetates like ethylacetate; organic nitriles like acetonitrile, benzonitrile; silicon fluids like polymethylphenyl siloxane or mixtures thereof; non reactive ionic liquids like 1-n-butyl-imidazolium trifluoromethanesulfonate, and 1-ethyl-3-methyl-imidazolium bis(trifluoromethyl sulfonyl)imide or a mixture thereof.

In a preferred embodiment of the present invention, the organic solvent is a homogeneous Brønsted catalyst characterized by a pKa equal to or lower than 5 and is selected from the group consisting of acetic acid, methanesulfonic acid, fluoromethanesulfonic acid, trifluoromethanesulfonic acid, trichloromethanesulfonic acid, trifluoroacetic acid, tert-butyl-sulfonic acid, p-toluenesulfonic acid, naphthalene sulfonic acid, 2,4,6-trimethylbenzene-sulfonic acid, perfluoro or perchloro sulfonic acids, perfluoro or perchloro carboxylic acids, phosphorous acid, phosphoric acid and mixtures thereof.

Advantageously in step a) the N,N'-bis(carboxymethyl)-2,5-diketopiperazine, in the presence of the acid catalyst, is dissolved in a solvent, wherein the resulting solution comprises between about 2% and about 30% by weight and preferably between about 4% and about 20% by weight of N,N'-bis(carboxymethyl)-2,5-diketopiperazine.

In order to dissolve the N,N'-bis(carboxymethyl)-2,5-diketopiperazine, in the presence of the acid catalyst, in the solvent it may be necessary to heat up the mixture of N,N'-bis(carboxymethyl)-2,5-diketopiperazine, catalyst and solvent to a temperature comprised between about 30° C. and about 90° C., more preferably between about 50° C. and about 80° C. under stirring. On the other hand ultrasounds may be used to accomplish the dissolution of the N,N'-bis(carboxymethyl)-2,5-diketopiperazine in the solvent/catalyst mix at ambient temperature.

Once N,N'-bis(carboxymethyl)-2,5-diketopiperazine dissolved in the solvent/catalyst mix, the P—O—P anhydride moiety comprising compound, preferably tetraphosphorus hexaoxide, and the solution comprising N,N'-bis(carboxymethyl)-2,5-diketopiperazine and the acid catalyst, standing at a temperature comprised between about 20° C. and about 90° C., are gradually mixed, under stirring, in such a way that, during the mixing, the temperature of the reaction mixture does not exceed about 120° C., preferably about 90° C. and more preferably about 80° C.

In an embodiment of the present invention, the P—O—P anhydride moiety comprising compound, preferably the tetraphosphorus hexaoxide, is gradually added, under optimal mixing conditions, to the solution comprising the N,N'-bis(carboxymethyl)-2,5-diketopiperazine and the acid catalyst, standing at a temperature comprised between about 20° C. and about 90° C., in such a way that the temperature of the reaction mixture does not exceed about 120° C., preferably about 90° C. and more preferably about 80° C.

In a preferred embodiment of the present invention, the solution comprising the N,N'-bis(carboxymethyl)-2,5-diketopiperazine, standing at a temperature comprised between about 20° C. and about 90° C., is gradually added, under optimal mixing conditions, to the P—O—P anhydride moiety comprising compound, preferably the tetraphosphorus hexaoxide, and the acid catalyst in such a way that the temperature of the reaction mixture does not exceed about 120° C., preferably about 90° C. and more preferably about 80° C.

In step a) the ratio of "moles of acid catalyst" to "equivalents of P—O—P anhydride moiety, having one P atom at the oxidation state (+III) and the other P atom at the oxidation state (+III) or (+V)" is at least about 0.01 and is preferably comprised between about 0.1 and about 10.0

In step a) the mole ratio of "acid catalyst" to "N,N'-bis(carboxymethyl)-2,5-diketopiperazine" is at least about 0.01 and is preferably comprised between about 0.05 and 25.0, more preferably between about 0.1 and about 20.

The equivalent ratio of N,N'-bis(carboxymethyl)-2,5-diketopiperazine to the P—O—P anhydride moiety in step a) is preferably comprised between about 0.2 and about 2.5, more preferably between about 0.3 and about 2.0 and even more preferably between about 0.5 and about 1.5.

The P—O—P anhydride moiety comprising compound is preferably tetraphosphorus hexaoxide. The molar ratio of N,N'-bis(carboxymethyl)-2,5-diketopiperazine to tetraphosphorus hexaoxide in step a) is comprised between about 0.4 and about 5.0, preferably between about 0.6 and about 4.0 and more preferably between about 1.0 and about 3.0.

The gradual mixing of the P—O—P anhydride moiety comprising compound, preferably tetraphosphorus hexaoxide, and the solution comprising N,N'-bis(carboxymethyl)-2,5-diketopiperazine and the acid catalyst is performed under thorough stirring. Once the mixing completed, the reactor content is stirred at a substantially constant temperature comprised between about 30° C. and about 120° C., preferably between about 40° C. and about 100° C. for a period of time comprised between about 10 minutes and about 72 hours and preferably between about 1 hour and about 30 hours.

During the reaction of the P—O—P anhydride moiety comprising compound with N,N'-bis(carboxymethyl)-2,5-diketopiperazine, carbon monoxide and the P—C moiety comprising compounds are formed in equimolar amounts.

During the conversion two moles of CO will be formed for each converted mole of N,N'-bis(carboxymethyl)-2,5-diketopiperazine. CO will leave the reaction mixture as a gas of very high purity. This CO gas can be used in many applications like e.g. as a fuel, in combination with hydrogen for methanol and Fischer-Tropsch hydrocarbons manufacture, for hydroformylation reactions, for alcohol carbonylation e.g. carbonylation of methanol to acetic acid or the conversion of methylacetate to acetic anhydride.

After completion of step a), the reaction mixture of step a), comprising the N,N'-bis(phosphonomethyl)-2,5-diketopiperazine, its dehydrated forms or their derivatives, are hydrolyzed in step b). This hydrolysis is advantageously performed under acidic, neutral or alkali conditions and preferably under acid conditions.

Preferably, water is added to the reaction mixture after it is cooled down to room temperature. Alternatively the reaction mixture can be cooled down through the addition of water. The hydrolysis is performed at a temperature comprised between about 25° C. and about 250° C., preferably between about 80° C. and about 200° C. for a period comprised between about 10 minutes and about 100 hours and preferably between about 1 hour and about 50 hours.

During the hydrolysis, the N,N'-bis(phosphonomethyl)-2,5-diketopiperazine, its dehydrated forms or their derivatives are converted into the N-(phosphonomethyl)glycine or its derivatives meanwhile the possible excess of P—O—P anhydride moieties is converted into P—OH moieties Unreacted P—O—P anhydride moieties may be the result from an incomplete conversion or from using a stoichiometric excess of P—O—P anhydride group comprising compounds.

EXAMPLES

The following examples illustrate the invention; they are merely meant to exemplify the present invention, but are not destined to limit or otherwise define the scope of the present invention.

Example 1

Synthesis of N,N'-bis(phosphonomethyl)-2,5-diketopiperazine

In a round-bottom flask equipped with a mechanical stirrer, a thermometer, a condenser 4.00 g (17.2 mmole) N,N'-bis(carboxymethyl)-2,5-diketopiperazine was mixed with 25 ml trifluoromethanesulfonic acid. Subsequently, the reaction mixture was heated to 75° C. and 1.89 g (8.6 mmole) tetraphosphorus hexaoxide was added slowly. Afterwards the reaction mixture was stirred for 16 hour at 75° C. During the addition and during the reaction time the evolution of carbon monoxide was observed. At ambient temperature 30 ml of water was added to the reaction mixture which subsequently was heated to 95° C. for 6 hour. A white solid precipitated that was removed by filtration at ambient temperature (yield: 4.35 g). The solid consisted of N,N'-bis(phosphonomethyl)-2,5-diketopiperazine at 98.9% by weight.
The overall yield for the isolated solid is determined as 83.2%.

In table 1 a series of examples, according to the present invention, is reported.
In this table:
Column 1: indicates the identification number of the example.
Column 2: indicates the number of mmoles of N,N'-bis(carboxymethyl)-2,5-diketopiperazine with into brackets the number of carboxylic acid milliequivalents.
Column 3: indicates the type of catalyst.
Column 4: indicates the number of mmoles of catalyst.
Column 5: indicates the number of mmoles of tetraphosphorus hexaoxide.
Column 6: indicates the ratio of mmoles of N,N'-bis(carboxymethyl)-2,5-diketopiperazine to mmoles of tetraphosphorus hexaoxide with into brackets the ratio of carboxylic acid milliequivalents of N,N'-bis(carboxymethyl)-2,5-diketopiperazine to mmoles of tetraphosphorus hexaoxide
Column 7: indicates the ratio of mmoles of catalyst to mmoles of N,N'-bis(carboxymethyl)-2,5-diketopiperazine with into brackets the ratio of mmoles of catalyst to carboxylic acid milliequivalents of the N,N'-bis(carboxymethyl)-2,5-diketopiperazine.
Column 8: indicates the ratio of mmoles catalyst to mmoles of tetraphosphorus hexaoxide.
Column 9: indicates the temperature (° C.) of the mixture comprising the N,N'-bis(carboxymethyl)-2,5-diketopiperazine and acid catalyst to which the tetraphosphorus hexaoxide is added; this temperature is maintained during the whole tetraphosphorus hexaoxide addition.
Column 10: indicates the temperature (° C.) and time (hrs) conditions of the reaction mixture upon completion of the tetraphosphorus hexaoxide addition.
Column 11: indicates the temperature (° C.) and time (hrs) conditions of the reaction mixture comprising water, for hydrolysis of N,N'-bis(phosphonomethyl)-2,5-diketopiperazine, its dehydrated forms or their derivatives and of unreacted tetraphosphorus hexaoxide
Column 12: indicates the reaction yield, in % by weight, as measured by $^{1}$H-NMR and $^{31}$P-NMR spectroscopy
In table 1,
(1): stands for the overall yield of solid N,N'-bis(phosphonomethyl)-2,5-diketopiperazine.
(2): stands for the yield of N,N'-bis(phosphonomethyl)-2,5-diketopiperazine as determined on the solution or on the crude material after removal of all volatiles.
(3): stands for the yield of N-(phosphonomethyl)glycine.
(4): Amberlyst 15 (in Ex. 7) stands for Amberlyst™ 15 (Rohm & Haas) and is a strongly acidic, sulfonic acid, macroreticular polymeric resin based on crosslinked styrene-divinylbenzene copolymer.
(5): AlOTf$_3$ stands for Aluminum trifluoromethanesulfonate.

TABLE 1

| Ex | COOH (mmole) | Catalyst | Cata (mmole) | $P_4O_6$ (mmole) | $\frac{COOH}{P_4O_6}$ | $\frac{Cata}{COOH}$ | $\frac{Cata}{P_4O_6}$ | $T_1$/time ° C./hrs | $T_2$/time ° C./hrs | $T_3$/time ° C./hrs | Yield (%) |
|---|---|---|---|---|---|---|---|---|---|---|---|
| 2 | 34.4 (68.8) | Trifluoromethanesulfonic acid | 566.0 | 17.2 | 2.0 (4.0) | 16.0 (8.0) | 32.9 | 75 | 75/16 | 25/24 | 27.0[1] |
| 3 | 17.2 (34.4) | Trifluoromethanesulfonic acid | 135.6 | 8.6 | 2.0 (4.0) | 7.9 (3.9) | 15.8 | 75 | 75/24 | 95/8 | 29.9[2] |
| 4 | 17.2 (34.4) | Trifluoromethanesulfonic acid | 282.5 | 8.6 | 2.0 (4.0) | 16.4 (8.2) | 32.8 | 65 | 75/4 | 25 | 26.6[2] |
| 5 | 8.6 (17.2) | Trifluoromethanesulfonic acid | 282.5 | 8.6 | 1.0 (2.0) | 8.2 (4.1) | 32.8 | 65 | 75/4 | 25 | 18.4[2] |
| 6 | 20.0 (40.0) | Amberlyst-15 [4] Acetonitrile (20 ml) | 9.8 | 10.0 | 2.0 (4.0) | 2.0 (1.0) | 1.0 | 25 | 70/7 | 25 | 0.2[2] |
| 7 | 20.0 (40.0) | Trifluoromethanesulfonic acid Acetonitrile (20 ml) | 10.0 | 10.0 | 2.0 (4.0) | 2.0 (1.0) | 1.0 | 25 | 80/7 | 25 | 18.4[2] |
| 8 | 20.0 (40.0) | Trifluoromethanesulfonic acid 1,4-dioxane (20 ml) | 10.0 | 10.0 | 2.0 (4.0) | 2.0 (1.0) | 1.0 | 25 | 100/5 | 25 | 0.9[2] |
| 9 | 20.0 (40.0) | Trifluoroacetic acid | 326.5 | 10.0 | 2.0 (4.0) | 16.3 (8.2) | 1.0 | 32.7 | 50/8 | 25 | 0.9[2] |
| 10 | 20.0 (40.0) | AlOTf3 [5] Acetonitrile (20 ml) | 2.0 | 10.0 | 2.0 (4.0) | 0.1 (0.05) | 0.5 | 25 | 70/6 | 25 | 2.4[2] |

TABLE 1-continued

| Ex | COOH (mmole) | Catalyst | Cata (mmole) | $P_4O_6$ (mmole) | $\dfrac{\text{COOH}}{P_4O_6}$ | $\dfrac{\text{Cata}}{\text{COOH}}$ | $\dfrac{\text{Cata}}{P_4O_6}$ | $T_1$/time °C./hrs | $T_2$/time °C./hrs | $T_3$/time °C./hrs | Yield (%) |
|----|--------------|----------|--------------|------------------|-------------------------------|-------------------------------------|--------------------------------|--------------------|--------------------|--------------------|-----------|
| 11 | 20.0 (40.0)  | Trifluoromethanesulfonic acid | 282.5 | 10.0 | 2.0 (4.0) | 14.1 (7.1) | 28.3 | 60 | 80/6 | 150/12 | 89.4[3] |

The invention claimed is:

1. A method for the synthesis of N-(phosphonomethyl) glycine or one of its derivatives selected from the group consisting of its salts, its phosphonate esters and its phosphonate ester salts, comprising the steps of:
   a) forming a reaction mixture comprising an acid catalyst, N,N'-bis(carboxymethyl)-2,5-diketopiperazine and a compound comprising one or more P—O—P anhydride moieties, wherein said moieties comprise one P atom at the oxidation state (+III) and the other P atom at the oxidation state (+III) or (+V), to form N,N'-bis(phosphonomethyl-2,5-diketopiperazine, its dehydrated forms or their phosphonate esters;
   b) hydrolyzing the reaction mixture to form N-(phosphonomethyl)glycine or one of its derivatives selected from the group consisting of its salts, its phosphonate esters and its phosphonate ester salts.

2. The method according to claim 1, wherein in step a), the compound comprising a P—O—P anhydride moiety, having one P atom at the oxidation state (+III) and the other P atom at the oxidation state (+III) or (+V), is gradually mixed, into a mixture comprising N,N'-bis(carboxymethyl)-2,5-diketopiperazine and an acid catalyst, while maintaining the temperature below 120° C., preferably below 90° C., more preferably below 80° C.

3. The method according to claim 1, wherein the P—O—P anhydride moiety comprising compound is selected from the group consisting of:
   tetraphosphorus hexaoxide, tetraethylpyrophosphite;
   the P—O—P—P anhydride moiety comprising compound obtained from the combination of one or more compounds comprising one or more P—OH moieties with one or more compounds comprising one or more P—O—P anhydride moieties, wherein the P atom of one or more compounds is at the oxidation state (+III);
   the P—O—P anhydride moiety comprising compound obtained from the combination of one or more compounds comprising one or more P—OH moieties with one or more compounds comprising one or more P—X moieties, wherein the P atom of one or more compounds is at the oxidation state (+III);
   the P—O—P anhydride moiety comprising compound obtained from the combination of one or more compounds having one or more P-X moieties and water, wherein the P atom of the P—X moiety comprising compound is at the oxidation stage (+III);
   the P—O—P anhydride moiety comprising compound obtained from the combination of one or more compounds having 2 or more P—O—P moieties and water, wherein the P—O—P moiety comprising compound has P atom at the oxidation state (+III) and one P atom at the oxidation state (+III) or (+V);
   wherein the compounds having one or more P—OH moieties may be accessible by tautomerization of a >P(=O)H moiety,
   wherein X is a halogenide selected from the group consisting of chlorine, bromine and iodine and,
   wherein the halogen level is 1,000 ppm or less, preferably 500 ppm or less and more preferably 200 ppm or less, expressed in relation to the P—O—P anhydride moiety comprising compound.

4. The method according to claim 1, wherein the P—O—P anhydride moiety comprising compound is selected from the group consisting of tetraphosphorus hexaoxide, tetraethylpyrophosphite, and the P—O—P anhydride moiety comprising compound obtained from the combination of phosphorous acid and tetraphosphorus hexaoxide, of phosphorous acid and tetraphosphorus decaoxide, of phosphorous acid and phosphorus trichloride, of dimethylphosphite and tetraphosphorus decaoxide, of phosphorus trichloride and water and of tetraphosphorus hexaoxide and water.

5. The method according to claim 1, wherein the P—O—P anhydride moiety comprising compound is tetraphosphorus hexaoxide.

6. The method according to claim 1, wherein the acid catalyst is a homogeneous Brønsted acid catalyst preferably selected from the group consisting of methanesulfonic acid, trifluoromethanesulfonic acid, acetic acid, trifluoroacetic acid, p-toluenesulfonic acid, hydrochloric acid, phosphorous acid, phosphoric acid and hypophosphorous acid and mixtures thereof.

7. The method according to claim 1, wherein the acid catalyst is a heterogeneous Brønsted acid catalyst selected from the group consisting of:
   (i) solid acidic metal oxide combinations as such or supported onto a carrier material;
   (ii) cation exchange resins selected from the group comprising copolymers of styrene, ethylvinyl benzene and divinyl benzene, functionalized so as to graft $SO_3H$ moieties onto the aromatic group and perfluorinated resins carrying carboxylic and/or sulfonic acid groups;
   (iii) organic sulfonic, carboxylic and phosphonic Brønsted acids (which are substantially immiscible in the reaction medium at the reaction temperature);
   (iv) an acid catalyst derived from:
      the interaction of a solid support having a lone pair of electrons onto which is deposited an organic Brønsted acid; or
      the interaction of a solid support having a lone pair of electrons onto which is deposited a compound having a Lewis acid site; or
      heterogeneous solids functionalized by chemical grafting with a Brønsted acid group or a precursor therefore; and
   (v) heterogeneous heteropolyacids of the general formula $H_xPM_yO_z$ wherein P is selected from phosphorus and silicon and M is selected from tungsten and molybdenum and combinations thereof.

8. The method according to claim 1, wherein the acid catalyst is a Lewis acid catalyst selected from the group consisting of $LiN(CF_3SO_2)_2$, $Mg(OCF_3SO_2)_2$, $Al(OCF_3SO_2)_2$, $Bi(OCF_3SO_2)_3$, $Sc(OCF_3SO_2)_3$.

9. The method according to claim 1, wherein the acid catalyst is trifluoromethanesulfonic acid.

10. The method according to claim 1, wherein the reaction mixture of step a) comprises a solvent selected from the group consisting of ethylacetate, acetonitrile, 1,4-dioxane, sulfolane, toluene, paraffin, aliphatic and aromatic halogenated hydrocarbons, such as tetrachloroethane, trichloroethylene, tetrachloroethylene, carbon tetrachloride, o-chlorotoluene, dichlorobenzene and monochloro benzene, 1-ethyl-3-methyl-imidazolium bis(trifluoromethyl sulfonyl)imide or a mixture thereof.

11. The method according to claim 1, wherein step a), after completion of the mixing of the compound comprising a P—O—P anhydride moiety, having one P atom at the oxidation state (+III) and the other P atom at the oxidation state (+III) or (+V), the N,N'-bis(carboxymethyl)-2,5-diketopiperazine, the acid catalyst and optionally the solvent, is maintained at a temperature comprised between 30° C. and 120° C., preferably between 40° C. and 100° C. for a period of time comprised between 10 minutes and 72 hours, preferably comprised between 1 hour and 30 hours.

12. The method according to claim 1, wherein the hydrolysis of step b) is performed under acid conditions at a temperature comprised between 25° C. and 250° C., preferably between 80° C. and 200° C. for a period of time comprised between 10 and 100 hours, preferably between 1 and 50 hours.

13. The method according to claim 1, wherein the equivalent ratio of N,N'-bis(carboxymethyl)-2,5-diketopiperazine to P—O—P anhydride moiety is comprised between 0.2 and 2.5, preferably between 0.3 and 2.0 and more preferably between 0.5 and 1.5.

14. The method according to claim 1, wherein the molar ratio of N,N'-bis(carboxymethyl)-2,5-diketopiperazine to tetraphosphorus hexaoxide is comprised between 0.4 and 5.0, preferably between 0.6 and 4.0 and more preferably between 1.0 and 3.0.

15. The method according to claim 1, wherein the molar ratio of the acid catalyst to the N,N'-bis(carboxymethyl)-2,5-diketopiperazine is comprised between 0.05 and 25.0, preferably between 0.1 and 20.0.

16. The method according to claim 1, wherein carbon monoxide is recovered and reused.

17. The method according to claim 1, wherein the derivatives are selected from the group consisting of N-(phosphonomethyl) glycine salts, phosphonate esters of N-(phosphonomethyl)glycine and phosphonate esters of N-(phosphonomethyl)glycine salts and wherein the cation of the salt is selected from the group consisting of ammonium, isopropylammonium, ethanolammonium, dimethylammonium, trimethylsulphonium, sodium and, potassium.

18. The method according to claim 1, wherein the N-(phosphonomethyl)glycine is obtained in a batch or a continuous process.

* * * * *

UNITED STATES PATENT AND TRADEMARK OFFICE
CERTIFICATE OF CORRECTION

PATENT NO.        : 9,150,599 B2
APPLICATION NO.   : 14/415687
DATED             : October 6, 2015
INVENTOR(S)       : Sebastian Burck et al.

It is certified that error appears in the above-identified patent and that said Letters Patent is hereby corrected as shown below:

In the Claims

Column 15, Line 39, Claim 3:

After "the" and before "anhydride moiety"
Delete "–P-O-P-P" and
Insert -- –PO-P --

Column 16, Line 64-65, Claim 8:
After "Mg(OCF$_3$SO$_2$)$_2$,"
Delete "Al(OCF$_3$SO$_2$)$_2$," and
Insert -- Al(OCF$_3$SO$_2$)$_3$, --

Signed and Sealed this
Twenty-eighth Day of June, 2016

Michelle K. Lee
*Director of the United States Patent and Trademark Office*